(12) United States Patent
Feltman

(10) Patent No.: US 10,780,044 B2
(45) Date of Patent: Sep. 22, 2020

(54) NATURAL AND ORGANIC DEODORANT AND METHOD OF MAKING THE DEODORANT

(71) Applicant: Jo Ann Feltman, Temperance, MI (US)

(72) Inventor: Jo Ann Feltman, Temperance, MI (US)

(*) Notice: Subject to any disclaimer, the term of this patent is extended or adjusted under 35 U.S.C. 154(b) by 91 days.

(21) Appl. No.: 16/246,033

(22) Filed: Jan. 11, 2019

(65) Prior Publication Data

US 2019/0365636 A1    Dec. 5, 2019

Related U.S. Application Data

(60) Provisional application No. 62/678,209, filed on May 30, 2018.

(51) Int. Cl.

| *A61K 8/9789* | (2017.01) |
| *A61Q 15/00* | (2006.01) |
| *A61K 8/9794* | (2017.01) |
| *A61K 8/92* | (2006.01) |
| *A61K 8/19* | (2006.01) |

(52) U.S. Cl.
CPC .............. *A61K 8/9789* (2017.08); *A61K 8/19* (2013.01); *A61K 8/922* (2013.01); *A61K 8/9794* (2017.08); *A61Q 15/00* (2013.01); *A61K 2800/30* (2013.01); *A61K 2800/77* (2013.01); *A61K 2800/805* (2013.01); *A61K 2800/874* (2013.01)

(58) Field of Classification Search
CPC ................................ A61K 8/19; A61K 8/9789
USPC ........................................... 424/65; 514/937
See application file for complete search history.

(56) References Cited

U.S. PATENT DOCUMENTS

| 4,440,742 A | 4/1984 | Marschner | |
| 8,574,554 B2* | 11/2013 | Kindel | A23F 3/405 424/49 |
| 8,663,611 B2* | 3/2014 | Alden-Danforth | A61Q 15/00 424/66 |
| 8,741,275 B2* | 6/2014 | Dente | C08K 5/092 424/76.1 |
| 8,778,320 B2* | 7/2014 | Hiramoto | C11D 3/0068 424/76.1 |
| 2005/0002872 A1* | 1/2005 | Katz | A61Q 15/00 424/47 |
| 2007/0202062 A1* | 8/2007 | Workman | A61K 36/738 424/66 |
| 2007/0251840 A1 | 11/2007 | Francis | |
| 2017/0087199 A1* | 3/2017 | Patron | A61K 36/81 |
| 2018/0325797 A1* | 11/2018 | Despert | A61K 8/19 |

FOREIGN PATENT DOCUMENTS

| CA | 1112575 A | 10/1978 |
| FR | 2818904 | 7/2002 |
| FR | 2818904 A1 * | 7/2002 |

OTHER PUBLICATIONS

"DIY Natural Deodorant . . . That Actually Works!—The Healthy Maven"https://www.thehealthymaven.com/diy-natural-deodorant-that-actually-works (Year: 2015).*
brendid.com all natural deodorant diy tutorial (Year: 2015).*
Makestuff.com Recipes for makign your own bath powder. (Year: 2002).*

* cited by examiner

*Primary Examiner* — Nina Bhat

(57) ABSTRACT

A method of making a natural antibacterial deodorant composition from the extract of Buchu leaf with arrowroot powder, sodium bicarbonate, witch hazel and aloe vera. The combination of these ingredients provide a natural deodorant that is safe and effective in eliminating bad odor, when the deodorant composition is applied to the body, the deodorant does not occlude the pores of the skin and permits sweating but is effective against malodors.

2 Claims, No Drawings

NATURAL AND ORGANIC DEODORANT AND METHOD OF MAKING THE DEODORANT

The invention relates to a new type of deodorant that prevents anti-bacterial growth and malodor under the armpits without the use of aluminum.

PROBLEM

Several years ago, I had to have two lymph nodes removed under my armpit because my armpit would become enlarged. I was told by my Doctor to never use deodorant with Aluminum. This was a problem because the deodorants that eliminated odor and sweat that worked for me, all had aluminum in them. I was told the aluminum in deodorant can possibly cause cancer by clogging pores which doesn't allow you to release your toxins. The aluminum free deodorants that I've tried never worked. No matter what deodorant I applied, my friends and family would comment on how bad my odor was, so I had to do something. I did my research and knew I needed something that prevented body odor through antibacterial and anti-fungal breakdown of perspiration under my armpits. During this time of research and making of the deodorant I began fasting and asked God to lead me in helping others and through quiet and prayer, God lead me to find what was needed for this deodorant. These findings lead me in a personal fulfilling way in helping others in the future.

SOLUTION

The deodorant needed to include simple ingredients that would be natural and organic without aluminum. I searched the internet for ingredients that would prevent stink I also would watch documentaries which lead to my discovery of Buchu leaf in my deodorant.

The first ingredient I chose was baking soda because it regulates pH balance, neutralizes and absorbs odors.

Second was arrowroot powder there was so much to learn the healing properties and how the natives would use it to treat those with injuries of wounds from poisonous arrows, hence the name. It absorbs, and controls moisture and it can also be used as a thickening agent and is used as a great base for body care formulations. The first time I made the deodorant it was so runny and would run down my arm. The container was a roll-on and the liquid would dry and end up a crusty dry mess. If I heated the water and arrowroot powder it thickened, this was the perfect execution.

The third ingredient was aloe and over the years I knew it would help with burns and healing I used it myself as a cooling agent for sunburns. There are times when I shave and get razor burns so I knew the Aloe would be a great addition. Aloe also is an antibacterial and prevents and reduces odor.

The fourth ingredient is witch hazel, it lowers Ph, kills bacteria and rids the skin of moisture.

The last and most important ingredient is the Buchu leaf. The Buchu leaf is often used in perfumes as fragrance. The leaf is also an antibacterial and has been used as a base to mask the malodor caused by microbial activity. The leaf is grown in Africa on one side of a mountain only and cannot be reproduced anywhere else. Numerous people have tried to reproduce this very special leaf by transplanting and growing in other areas of the globe but have been unsuccessful. They're other benefits such reduces inflammation and as an insect repellent, gout, prevents bacteria, used for cleaning wounds and many other medicinal uses. The indigenous people of this area 100 years ago would trade a cap full of Buchu leaf for a sheep. Because this is so I believe that God has placed this special leaf and touched it to allow us to be able to enjoy its benefits which has been lost over the years.

In conclusion after learning of all this and more I knew this was the perfect combination of ingredients. Voila! The deodorant was made except one more thing needed to be added, preferably the essential oil allows for different scents that could make this a more marketable product.

The present invention seeks to provide a solution by providing clean, anti-fungal, anti-bacterial in a more natural and organic way to prevent bad odor for the user. I've worked diligently on this patent to obtain a balance of these ingredients, so they work well together in eliminating odor in a safe and effective way. The remarkable thing about this deodorant is I feel it could help numerous people like me searching for a deodorant without aluminum and it really works!

| Deodorant is comprised of: | Percentage Amounts |
| --- | --- |
| 16-20 Ounces of Distilled water | 65.800% |
| 3-5 Ounces of Witch Hazel | 15.628% |
| 2-4 Tablespoons of Baking Soda | 9.048% |
| 3-5 Tablespoons of Arrowroot Powder | 4.935% |
| 2-4 Tablespoons of Aloe Vera | 4.113% |
| 1-3 Tablespoons of Buchu leaf | 0.411% |
| 10 drops 100% Essential Oils (Fragrance) | 0.65% |

The invention claimed is:

1. A method of making an antibacterial and deodorant composition comprising of these steps of:
   a. providing a clean pot, adding to said pot 64-75% distilled water and 0.25-1% buchu leaves;
   b. steeping the buchu leaves in said distilled water to provide a buchu extract;
   c. adding to the buchu extract 4-9% arrowroot powder followed by mixing and heating to provide a thickened buchu composition;
   d. cooling said thickened buchu composition;
   e. adding to the cooled thickened buchu composition 7-12% by weight of sodium bicarbonate, 12-17% of witch hazel, 3-8% of aloe vera and 0.1-2% essential oils;
   f. mixing and blending in an electric mixer the composition of step e. to provide an antibacterial and deodorant composition;
   g. transferring said antibacterial and deodorant composition into a storage container;
   h. cooling the stored container of antibacterial and deodorant composition in a refrigerator to provide a liquid deodorant composition.

2. An antibacterial and deodorant composition consisting of:
   64-75% by weight distilled water;
   0.25-1% by weight buchu extract;
   4-9% by weight arrowroot powder;
   7-12% by weight sodium bicarbonate;
   12-17% by weight witch hazel;
   3-8% aloe vera; and
   0.1-2% by weight essential oils.

* * * * *